United States Patent [19]

Tomomatsu

[11] 4,043,187
[45] Aug. 23, 1977

[54] METHOD OF MEASURING SURFACE ROUGHNESS

[75] Inventor: Kenichi Tomomatsu, Kawasaki, Japan

[73] Assignee: Doryokuro Kakunenryo Kaihatsu Jigyodan, Tokyo, Japan

[21] Appl. No.: 733,022

[22] Filed: Oct. 15, 1976

[30] Foreign Application Priority Data

Oct. 16, 1975 Japan .................................. 50-124719

[51] Int. Cl.² .............................................. G01B 5/28
[52] U.S. Cl. ..................................................... 73/105
[58] Field of Search ................... 73/104, 105; 264/225

[56] References Cited

U.S. PATENT DOCUMENTS 2,601,703  7/1952  Sawyer .......................... 264/225 X

FOREIGN PATENT DOCUMENTS 358,378  10/1931  United Kingdom ................... 73/104

OTHER PUBLICATIONS

V. P. Butin-"Ndt by the Replica Method" - *Non-Destructive Testing* - vol. 3, No. 3, June 1970, pp. 173-176.

*Primary Examiner*—Charles A. Ruehl
*Attorney, Agent, or Firm*—Wenderoth, Lind & Ponack

[57] ABSTRACT

A method of measuring surface roughness of an object indirectly according to a tracer method by forming two different kinds of replicas. The first replica is made of a flexible material which can be easily stripped off from either the object surface or from the surface of the second replica. The second replica is made of a material with high hardness so that it will not suffer from any scratch or flaw from the tracer even when it hits the replica. Surface configuration of the object to be measured is transferred to the first replica and the surface configuration of the first replica is then transferred to the second replica, and surface roughness of this second replica is measured with a tracer.

3 Claims, No Drawings

1

METHOD OF MEASURING SURFACE ROUGHNESS

BACKGROUND OF THE INVENTION

This invention relates to a method for measuring surface roughness according to a tracer method, and more particularly it relates to a method for measuring surface roughness of an object indirectly by making two different kinds of replicas successively and measuring surface roughness of the second replica.

The term "surface roughness" means unevenness or ruggedness present of the surface of an object at narrow spacing, and the configuration or the condition of distribution of such surface roughness varies widely depending on the working process or surface treatment method used on the object.

There are known generally two different types of methods for measuring surface roughness: a direct tracer method in which surface roughness of the object is measured directly with a tracer, and an optical method in which light rays are applied to the object surface and its roughness is measured optically by way of reflection or interference of the light rays applied.

According to the optical method, it needs to make replicas of the object to be measured and also, in many cases, evaporation of metal on the replica surface is required for enhancing reflexibility of the replica surface. On the other hand, the tracer method involves the problem that scratches or flaws might be given to the object surface by the tracer, and this method is also subject to dimensional restriction by the tracing apparatus employed, so that this method may prove useless in certain specific applications, for example measurement of the internal wall surface of a fine tube. Further, the optical method is intended for measurement of a minute portion by use of a microscope, so that although this method is suited for measurement of a limited area, it is hardly possible with this method to correctly know the general trend or distribution of roughness on a large-sized object.

SUMMARY OF THE INVENTION

In view of the above, I have developed a novel method for measuring surface roughness of an object indirectly according to a tracer method by making replicas on two steps from the object surface and measuring the surface of the second replica with a tracer.

According to the method of my invention, a first replica of the surface of an object to be measured is prepared by applying a replica material with good releasability on said object surface to form a replica film thereon and then stripping it off from said object surface. Then a synthetic resin of the type which has high hardness when hardened is deposited on the surface of said first replica and, after hardening, said first replica is separated to thereby obtain a second replica, and surface roughness of this second replica is measured by using a tracer, thus indirectly determining surface roughness of the object. Ruggedness on the object surface is transferred accurately to the second replica surface. Since this second replica surface is high in hardness, there is no risk of giving scratches or flaws to this replica surface or affecting accuracy of measurement during the measuring operation.

It is therefore an object of this invention to provide a method of measuring surface roughness by use of a tracer.

Another object of this invention is to provide a surface roughness measuring method whereby it is possible to easily measure surface roughness of even such a location where access of the tracer is difficult, such as for example the internal wall surface of a fine or small diameter tube.

Still another object of this invention is to provide a method which is capable of measuring with ease surface roughness of even a soft and easily scratched type of object without inflicting any scratch or flaw to the object.

Yet another object of this invention is to provide a method whereby it is possible to obtain replicas with high precision of reproducibility and high hardness, allowing measurement of surface roughness with high accuracy according to a tracer method.

A further object of this invention is to provide a replica forming method which is far less expensive and more simple than the conventional optical method using vacuum evaporation.

DESCRIPTION OF THE PREFERRED EMBODIMENT

In the present invention, there are used two different kinds of replica material. The material used for the first replica is the one which has high stretchability and can be easily stripped off either from the object surface or from the second replica surface, and such material may, for instance, be a silicone rubber (such as prepared from Toray Silicone SH9550RTV (commercial name) manufactured by Toray Industries Inc., Japan). The material for the second replica is a synthetic resin with high hardness so that it will not get scratches or flaws from the tracer even when the latter hits the replica, and a preferred example of such resin is the one prepared by mixing an epoxy resin such as bisphenol A type epoxy resin with a hardening agent such as an aliphatic polyamine. In order to obtain speedy hardening, an accelerating agent may be added to the mixture of an epoxy resin and a hardening agent. The suitable mixing ratio of an epoxy resin, a hardening agent and an accelerating agent is, for example, 20 : 2 : 1.

According to the method of this invention, silicone rubber, or the material for the first replica, is applied on the surface of an object to be measured, and after hardened, the layer of said material is peeled off to make the first replica. Ruggedness on the object surface is transferred with high fidelity to the surface of the first replica. Then, an epoxy resin added with a hardening agent and an accelerating agent in the suitable ratios such as above-mentioned is applied on said first replica surface, and after said resin has hardened, the first replica is stripped off, thereby forming the second replica. Ruggedness of the first replica surface is thus precisely transferred to the surface of the second replica. Accordingly, the rugged surface condition of the object is reproduced faithfully on the surface of the second replica. Therefore, surface roughness of the object can be determined by measuring the surface of the thus obtained second replica with a tracer.

Various known methods may be employed for performing such measurement. For instance, it is possible to use a method in which the vertical movement of the tracer or feeler is converted into an electric quantity to determine the mean value of roughness, or a method in which the tracer movement is magnified by using a mechanical or optical lever or electrical means to record such movement in the form of roughness curve and the thus recorded curve is analyzed to know various factors relating to surface roughness.

The second replica used in this invention has Shore hardness of 34 to 60 and can well withstand the use conditions in the tracer method. Comparisons between surface roughness of the second replica and that of the object by use of a surface roughness tester and a microscope showed almost no difference therebetween, attesting almost perfect reproducibility of the replicas. Tolerances of reproducibility are less than about 4% for around 1 micron roughness, and such tolerances can be held closer for the greater sizes of roughness: they are substantially 0% for around 10 micron roughness.

It is apparent that the present invention can be embodied in various other forms without departing from the scope and spirit of this invention, and hence this invention is not limited in its scope by the specific embodiments described but defined merely by the appended claims.

What is claimed is:

1. A method of measuring surface roughness comprising the steps of applying a replica material with good releasability on the surface of an object to be measured to form a replica film on said surface, stripping off said replica film to thereby form a first replica, applying on the surface of said first replica a layer on a non-hardened synthetic resin of the type which becomes high in hardness when hardened, separating said first replica after hardening of said resin to form a second replica, and measuring roughness of the surface of said second replica with a tracer.

2. A method claimed in claim 1, wherein the material of the first replica is a silicone rubber.

3. A method claimed in claim 1, wherein the material of the second replica is an epoxy resin.

* * * * *